(12) United States Patent
Anitua Aldecoa

(10) Patent No.: US 8,992,219 B2
(45) Date of Patent: Mar. 31, 2015

(54) METAL STRUCTURE THAT SERVES AS AN INTERNAL SUPPORT TO A DENTAL PROSTHESIS

(71) Applicant: Biotechnology Institute, I MAS D, S.L., Vitoria (ES)

(72) Inventor: Eduardo Anitua Aldecoa, Vitoria (ES)

(73) Assignee: Biotechnology Institute, I MAS D, S.L., Vitoria (Alava) (ES)

( * ) Notice: Subject to any disclaimer, the term of this patent is extended or adjusted under 35 U.S.C. 154(b) by 0 days.

(21) Appl. No.: 13/731,376

(22) Filed: Dec. 31, 2012

(65) Prior Publication Data
US 2013/0171586 A1 Jul. 4, 2013

(30) Foreign Application Priority Data

Dec. 29, 2011 (ES) .................................. 201101373

(51) Int. Cl.
*A61C 13/225* (2006.01)
*A61C 8/00* (2006.01)
(52) U.S. Cl.
CPC .............. *A61C 8/0027* (2013.01); *A61C 8/0048* (2013.01)
USPC .......................... 433/172; 433/173; 433/199.1
(58) Field of Classification Search
CPC .................. A61C 8/0027–8/28; A61C 8/0048; A61C 8/0053–8/0054; A61C 13/275; A61C 13/2656
USPC ........ 433/172–176, 201.1, 199.1, 200.1, 214, 433/180–183, 190–191, 193–195, 433/206–211; 623/17.17–17.19
See application file for complete search history.

(56) References Cited

U.S. PATENT DOCUMENTS

| 5,219,286 A * | 6/1993 | Hader ........................... 433/172 |
| 6,905,336 B2 * | 6/2005 | Summers ...................... 433/214 |
| 2007/0281283 A1 * | 12/2007 | Lundgren ..................... 433/214 |
| 2012/0189985 A1 * | 7/2012 | Iglesias ......................... 433/174 |

FOREIGN PATENT DOCUMENTS

| CH | 699904 B1 * | 5/2010 |
| WO | WO 2011/035398 A1 * | 3/2011 |

* cited by examiner

*Primary Examiner* — Edward Moran
(74) *Attorney, Agent, or Firm* — Browdy and Neimark, PLLC

(57) ABSTRACT

Metal structure that serves as an internal support to a dental prosthesis, comprising at least two support posts (1) designed to be attached on respective dental implants (10), and at least one rod (3) for connecting two adjacent support posts (1), where at least one support post (1) comprises at least one protruding element (4*a*, 4*b*) that projects from its side, and at least one rod (3) that comprises a first end (5) provided with a blind hole (6) designed to receive a first protruding element (4*a*) of a support post (1), thus providing an articulated connection that acts like a ball joint, and a longitudinal recess (7) designed to receive a second protruding element (4*b*) of the adjacent support post (1). This structure is easy to prepare and to assemble.

14 Claims, 4 Drawing Sheets

METAL STRUCTURE THAT SERVES AS AN INTERNAL SUPPORT TO A DENTAL PROSTHESIS

TECHNICAL FIELD

The invention refers to a metal structure that serves as an internal support or frame to a dental prosthesis.

PRIOR ART

Dental implantology is a medical technique that allows the placing of artificial dental prostheses in the patients' mouth by using osseointegrated dental implants as a support. To this end, one or more dental implants are installed in the patient's mouth, and subsequently, a prosthesis of varying size and complexity is designed that is connected to said dental implant or implants.

The process of planning and constructing a dental prosthesis destined to be mounted on dental implants basically comprises the following steps. First, the dental prosthesis is planned by studying the patient's shape of mouth and teeth, in order to obtain after a more or less complex process an impression of the final external shape of the artificial teeth and the position in which they are to be placed. Then follows the designing and constructing of the dental prosthesis. The dental prosthesis basically consists of two parts: an internal metal structure that serves as a support, and is generally made of titanium, cobalt chromium, zirconium, noble alloys (AU, PD), semi-noble or base alloys applied in the dental sector; an external coating or external visible part that provides the external finish of the dental prosthesis, resembling real teeth, and that is generally made of acrylic, composite or porcelain. Usually, a layer of opaque material is applied between the metal structure and the external coating in order to cover the metallic colour of the metal structure so that the external coating is not darkened by the metal structure underneath.

There are currently various techniques to design and construct the metal structure, amongst which there are two that generally stand out: a traditional manual technique and an advanced software-aided technique.

The traditional manual technique basically consists in temporally connecting provisional titanium cylinders to the dental implants and subsequently interconnecting the adjacent provisional cylinders by means of a titanium rod. The titanium rods are manually cut to the required length and are soldered to the provisional cylinders by means of laser welding. This technique has the advantage of being relatively easy to comprehend and execute. On the other side, the technique has some drawbacks: it requires a laser machine, which is generally expensive and unavailable in many laboratories, and it requires specialized staff that is able to handle a machine of this type. This manual technique allows the construction of metal structures for supporting acrylic or composite coatings, which do not require high temperature treatments as is the case with porcelain coatings (in high temperatures the metal structure may suffer alterations).

In the advanced technique, the complete process for planning the restoration and manufacturing of parts (including the mechanization of the metal structure and the external coating or dental prosthesis) is performed as a CAD/CAM process, i.e., a completely automated, computer-aided process. This technique allows the construction of metal structures suitable for any kind of coating material. The CAD/CAM procedures have many advantages, most important of which is that they provide restorations of high precision and quality. Nonetheless, they also have notable disadvantages, such as requiring a significant investment due to the high cost of the machines and software involved and the need for a highly qualified staff for handling said machines and software.

The objective of the present invention is to offer a metal structure that is manually manufactured and assembled, which provides an easier and faster manufacturing and assembly method compared to the method provided by traditional metal structures based on provisional cylinders and laser welded rods, in a way that metal structures may in general be manufactured by any dental technician without the need of specialized qualification, and in any prosthetics laboratory. At the same time, the passive fit and other qualities of the metal structure according to the invention shall equal or even surpass the traditional metal structures.

BRIEF DESCRIPTION OF THE INVENTION

The object of the invention is a metal structure that serves as an internal support to a dental prosthesis, where said metal structure, just as traditional metal structures, comprises at least two support posts arranged along respective longitudinal axes in order to be attached on respective dental implants, and at least one rod for connecting two adjacent support posts. The metal structure according to the invention presents the particularity that at least one support post comprises at least one protruding element that projects from the outer surface of a side of the support post. At the same time, at least one rod comprises a first end provided with a blind hole designed to receive a first protruding element of a support post, thus providing an articulated connection that acts like a ball joint, and a longitudinal recess designed to receive a second protruding element of the adjacent support post (after the rod has been cut to the required length).

In this way, the connection between support posts is carried out through rods, of which one end is articulately connected (as a ball joint connection) to a protruding element of a support post. The rods are then cut to the required length and attached to a protruding element of another support post, and so forth.

This metal structure is designed to address provisional cases, including the so-called cases of "immediate use" (wherein a prosthesis is made for the same day). Thus, the support post is usually called provisional cylinder (although the invention is not to be limited in that the support post necessarily is cylindrical or provisional). Additionally, the structure provided by the invention is suitable for acrylic or composite coatings. The use of acrylic coatings is considered especially advantageous, as the hot mixture of acrylic materials applied over the metal structure is able to fill in the gaps and hollow spaces of the metal structure, thus rendering the assembly more rigid.

The metal structure according to the invention has numerous advantages. Not only does it allow for a particularly speedy construction of the metal structure, as it simplifies the carrying out of the connection of the two rods' ends, but it also requires a smaller initial investment compared to traditional, laser-welded metal structures, as no laser welding is required and therefore no laser machine is needed. This enables smaller laboratories, which often lack the full equipment that is required, to be able to manufacture and assemble the metal structure according to the invention. An additional advantage is that the prosthetics technician does not need to be a trained specialist in this area, as the connections of the rod are easily executed. Furthermore, the metal structure according to the invention allows for a good passive fit of the dental prosthesis on the dental implants, as there are no stress elements (due to the lack of welding points).

Other objects of the invention are separately the support post and the rod that are comprised in the metal structure of the invention.

BRIEF DESCRIPTION OF THE DRAWINGS

Details of the invention are depicted in the accompanying figures, which are intended to be illustrative and non-limiting.

DETAILED DESCRIPTION OF THE INVENTION

Figure 1:
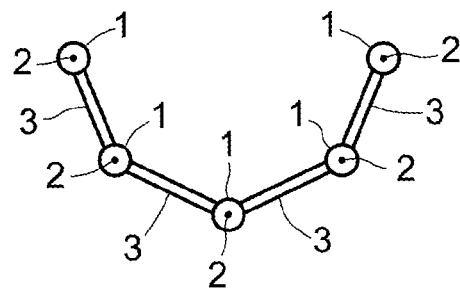
FIG. 1 shows a very schematic top view of a metal structure that is provided with various support posts and connection rods between them, according to both conventional techniques and the present invention.

FIG. 1 shows a very schematic top view of a metal structure that serves as an internal support to a dental prosthesis, manufactured in accordance with traditional techniques or according to the present invention. As can be observed, the metal structure comprises a series of support posts (1) arranged along respective longitudinal axes (2) in order to be attached to respective dental implants (not visible in the present figure), and a series of rods (3) interconnecting the adjacent support posts (1).

Figure 2:
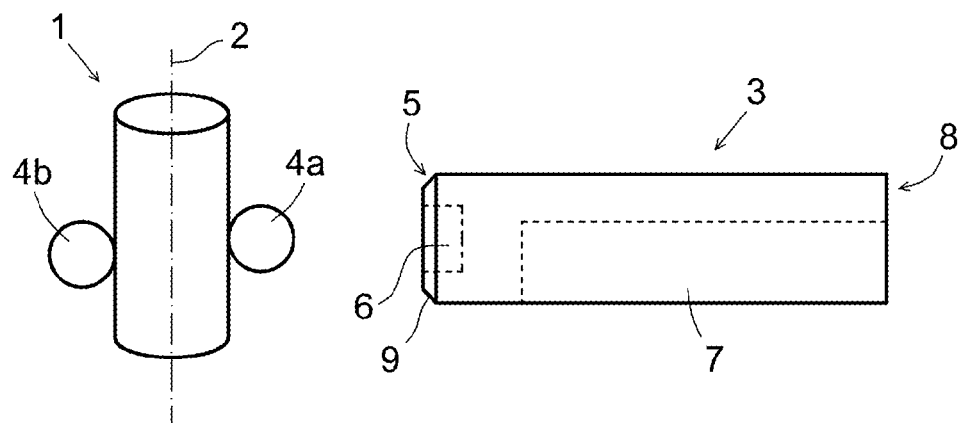
FIG. 2 shows one embodiment of the support post and the rod comprised in the metal structure according to the invention.
Figure 9:
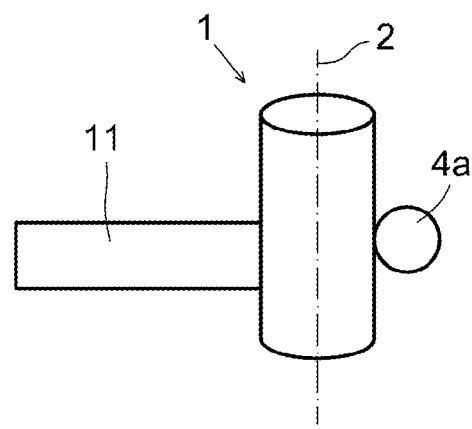
FIG. 9 shows a schematic view of a second embodiment of the metal structure's support post according to the invention.
Figure 3:
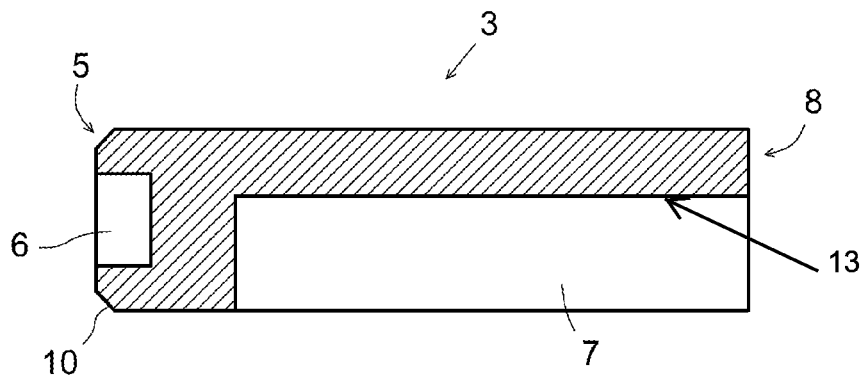
FIG. 3 shows a cross-sectional view of the rod depicted in FIG. 2.
Figure 5:
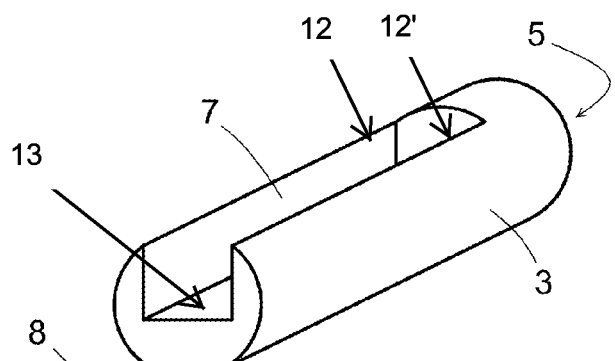

FIG. 2 shows one embodiment of the support post (1) and the rod (3) comprised in the metal structure according to the invention. The support post (1) according to the invention comprises at least one protruding element (4a, 4b) that projects from the outer surface of a side of the support post (1). In the represented embodiment, the support post (1) comprises in particular two protruding elements (4a, 4b), which are also spherical in shape. Furthermore, the rod (3) according to the invention comprises a first end (5) provided with a blind hole (6) designed to receive a first protruding element (4a) of a support post (1), thus providing an articulated connection with said first protruding element (4a) acting as a ball joint. The rod (3) further comprises a longitudinal recess (7) designed to receive a second protruding element (4b) of the adjacent support post (1) (not depicted). The longitudinal recess (7) has two sidewalls (12) and an inner longitudinal ceiling (13), as shown in FIGS. 3 and 5.

Preferably, the longitudinal recess (7) extends all the way to the second end (8) of the rod (3), as shown in the figure. This embodiment, with the recess extending until the second end (8), allows the rod (3) to be easily machined, i.e. it makes the manufacturing of the rod (3) easier and less expensive.

Preferably, the first end (5) of the rod (3) presents a recess (9), i.e. it has not a squared edge, in order to help the movement of the connection to act as a ball joint between the first protruding element (4a) and the blind hole (6). In the represented embodiment, said recess (9) has a conical shape.

In the represented embodiment, the support post (1) comprises two protruding elements (4a, 4b) that project from the outer surface of the support post (1), where said protruding elements (4a, 4b) are arranged opposite of one another, one on each side of the longitudinal axis (2) of the support post (1). This type of support post (1) is generally used in intermediate points of the metal structure, i.e. any point that does not include the ends of said structure, as it allows for the connection of a rod (3) to each side of the support post (1).

In this embodiment, the protruding elements (4a, 4b) are preferably arranged on different heights with regard to the base of the support post (1), as shown in FIG. 2. This makes the support post (1) more versatile and may also serve for more clinical cases: it should be taken into account that the distance between the implant and the gum may vary, and that occasionally the support post must be attached to an implant even on a subgingival level (beneath the gum line).

Figure 4:
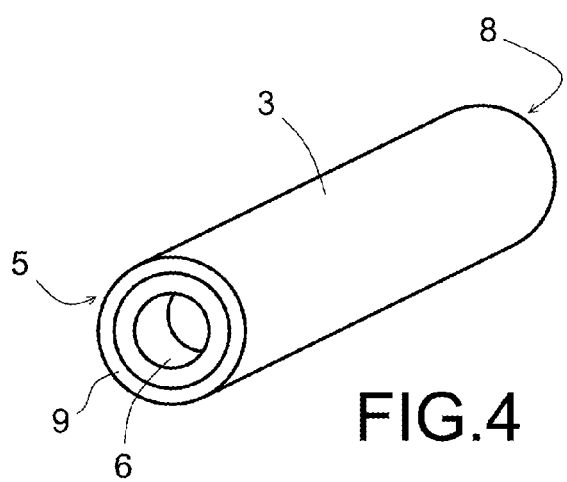
FIGS. 4 and 5 show two perspectives of the rod depicted in FIG. 2.

FIGS. 3 to 5 show different views of the described rod (3), and are intended to facilitate a comprehensive understanding of the part.

Figure 6:
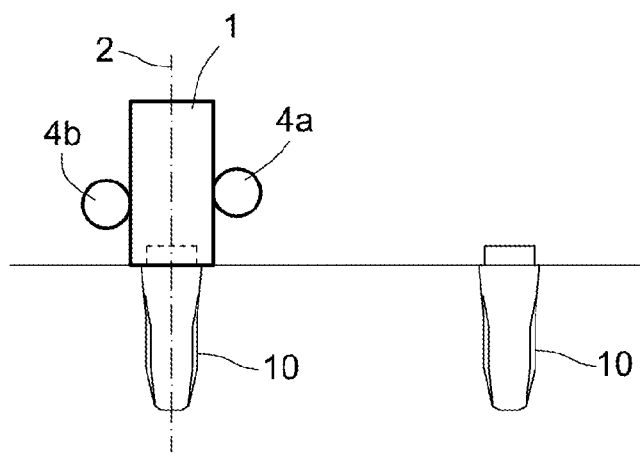
FIGS. 6 to 8 show the sequence of construction and assembly of the metal structure depicted in the previous figures.
Figure 7:
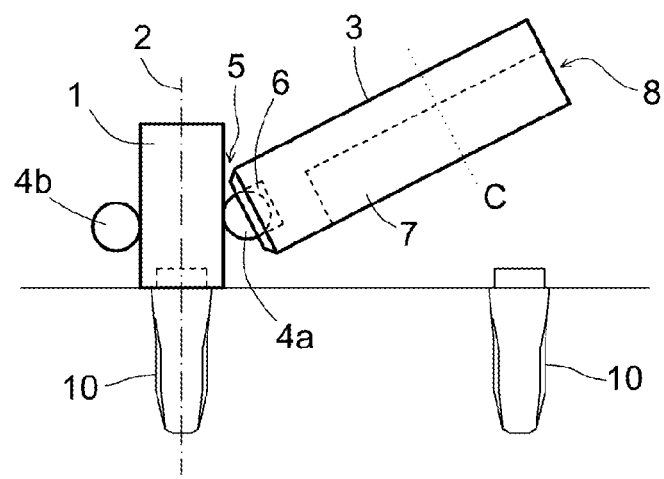
Figure 8:
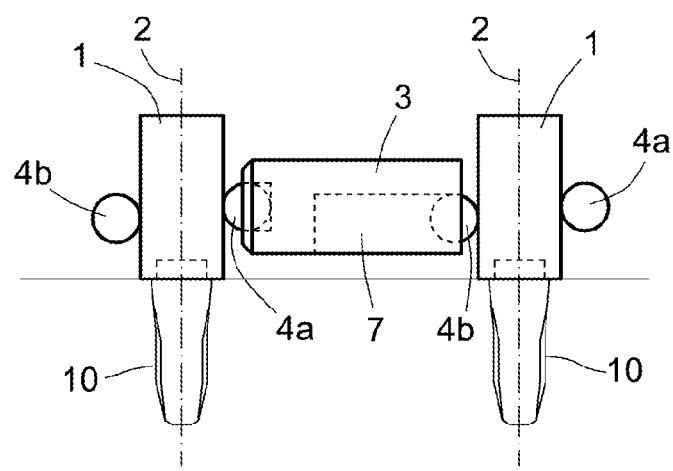

FIGS. 6 to 8 show the sequence of assembly of the metal structure according to the invention. First, as shown in FIG. 6, a first support post (1) is mounted (usually by being screwed in) on a dental implant (10). Then, as shown in FIG. 7, the first end (5) of a first rod (3) is approached to the support post (1) until the first protruding element (4a) of the support post (1) is lodged in the blind hole (6) of the first end (5) of the rod (3). This socket acts as a ball joint, creating an articulated connection between the support post (1) and the rod (3). Next, the rod (3) is cut to the required length (marked with the letter C). Afterwards, as shown in FIG. 8, a second support post (1) is mounted on the adjacent dental implant (10), and the rod (3) is easily lowered down, in a way that a second protruding element (4b) of the recently mounted support post (1) is lodged in the longitudinal recess (7) of the rod (3). This easy process will provide a section of the structure between two adjacent support posts (1), and by continuing, it will successively create the rest of the sections. Once the assembly is completed, the elements are fixed by applying cianocrilate, cement, chemical adhesive or any other applicable fixative. The next step, once the metal structure is completed, would generally include processes that are also included in traditional processes, such as the sandblasting with aluminium oxide at a pressure of 2 bar, in order to produce an abrasion on the surface of the metal and thus create mechanical microretentions on the surface, the application of an opaque material, the coating with an acrylic material and the shaping of the dental pieces.

In an alternative to the support post (1) represented in the figures, the support post (1) may comprise only a first protruding element (4a), which would result especially interesting for support posts (1) positioned at the outer ends of the metal structure, as they only need to be connected to one rod (3). In this case, the outer support posts (1) preferably comprise an additional solidary rod (11) without any kind of articulation, forming a single element with the rest of the support post (1). Said solidary rod (11) is located on the free side, i.e. on the opposite side of the first protruding element (4a), or in other words, the solidary rod (11) and the first protruding element (4a) are arranged one on each side of the longitudinal axis (2) of the support post (1). The solidary rod (11) allows attaching a last artificial dental piece on top of the same, without any risk of said dental piece getting broken during the use of the dental prosthesis.

Figure 10:
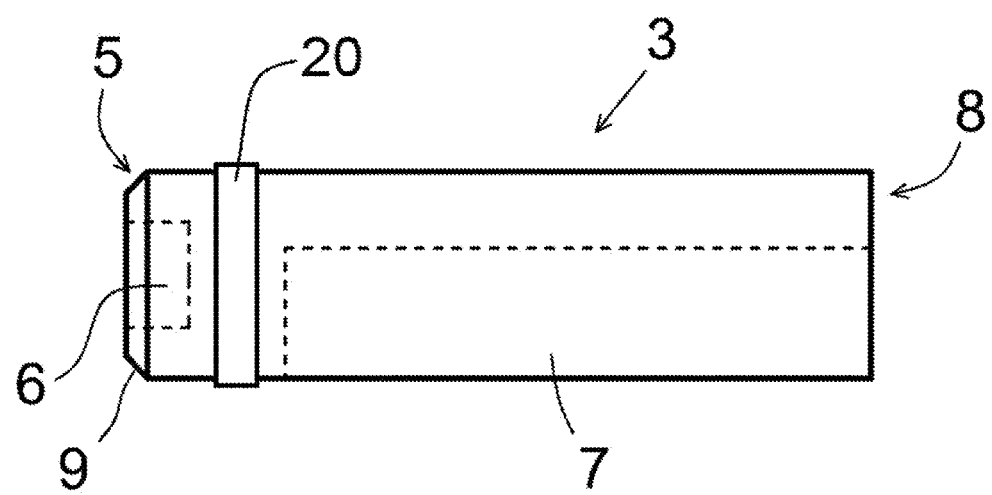
FIG. 10 shows a cross-sectional view of the rod depicted in FIG. 2, according to another embodiment of the invention.

In another embodiment different to the one represented, the rod (3) is not a single piece, but it comprises at least two segments that are joined by an intermediate articulated connection (20). The articulated connection (20) is shown schematically in FIG. 10.

The invention also contemplates other variants or embodiments different to the ones represented in the figures. By way of example, the geometrical shape of the protruding element (4a, 4b), which has been represented in the figures as a complete sphere, may also take other forms (ellipsoid, part of a sphere, etc.). The blind hole (6) that has been represented in a cylindrical shape, may present any applicable geometry as long as it allows the rotation of the first protruding element (4a) inside said blind hole (6). It is also contemplated that the rod (3) that has been represented in the figures with an external substantially cylindrical form, may also present any applicable geometry. The longitudinal recess (7) has been represented with flat inner faces, but it may present any applicable geometry, as long as it allows the second protruding element (4b) to be lodged inside said longitudinal recess (7).

Following are some examples of measurements to be considered for a metal structure with optimal performance. Thus, in a specific embodiment, the support post (1) has a height of 12 mm and the protruding elements (4a, 4b) have a spherical shape with a diameter of 2 mm. The first protruding element (4a) and the second protruding element (4b) have respectively a distance of 4 to 5 mm from the base of the support post (1). As for the rod (3), the blind hole (6) has a cylindrical shape with a depth of 1.3 mm and a diameter of 2 mm, and the longitudinal recess (7) starts at a distance of at least 1.8 mm from where the blind hole (6) ends, with a length of 10.9 mm and flat inner faces with a height of 2 mm and a width of 2 mm.

The invention claimed is:

1. A dental system comprising a metal structure and a dental prosthesis, said metal structure comprising at least two support posts (1) arranged along respective longitudinal axes (2) to be attached on respective dental implants (10), and at least one rod (3) for connecting the two adjacent support posts (1), wherein:
   the at least two support posts each (1) comprise a first and a second protruding element (4a, 4b) that project from the outer surface of a side of the support posts (1);
   the at least one rod (3) comprises a first end (5) and a second end (8), wherein the first end (5) comprises a longitudinal blind hole (6) designed to receive the first protruding element (4a) of a support post (1), thus providing an articulated connection that acts like a ball joint, and a longitudinal recess (7) extending to the second end (8) designed to receive the second protruding element (4b) of the adjacent support post (1),
   wherein said longitudinal recess (7) is delimited by two longitudinal sidewalls and an inner longitudinal ceiling, said inner longitudinal ceiling providing a stop surface for the rod (3) second end (8) to become supported on the second protruding element (4b),
   wherein the longitudinal recess (7) extends from the second end (8) to an ending point that is closer to the first end (5) than to the second end (8); and wherein the dental prosthesis is supported by the metal structure.

2. The dental system, according to claim 1, wherein the rod (3) comprises at least two segments that are joined by an intermediate articulated connection.

3. The dental system, according to claim 1, wherein the first end (5) of the rod (3) has a conical portion (9) in order to help the movement of the connection to act as a ball joint between the first protruding element (4a) and the blind hole (6).

4. The dental system, according to claim 1, wherein each of the support posts (1) comprise two protruding elements (4a, 4b) that project from the outer surface of the support posts (1), where said protruding elements (4a, 4b) are arranged opposite of one another, one on each side of the respective longitudinal axes (2) of the support posts (1).

5. The dental system according to claim 4, wherein the protruding elements (4a, 4b) are arranged on different heights with regard to a respective base of each of the support posts (1).

6. A dental system comprising a metal structure and a dental prosthesis, said metal structure comprising:
   a first support post, arranged along a longitudinal axis, and comprising a first protruding element protruding from an outer surface of a side of said first support post;
   a second support post, arranged along a longitudinal axis, and comprising a second protruding element protruding from an outer surface of a side of said second support post, wherein
   said first and second support posts are to be attached on respective dental implants; and
   at least one rod for connecting said first and second support posts, said rod comprising a first end and a second end, wherein the first end comprises a longitudinal blind hole designed to receive the first protruding element of the first post, thus providing an articulated connection that acts like a ball joint, and a longitudinal recess extending to the second end, said longitudinal recess designed to receive said second protruding element of the second post, wherein
   said longitudinal recess is delimited by two longitudinal sidewalls and an inner longitudinal ceiling, said inner longitudinal ceiling providing a stop surface for the rod second end to become supported on the second protruding element,
   wherein the longitudinal recess extends from the rod second end to an ending point that is closer to the rod first end than to the rod second end; and wherein the dental prosthesis is supported by the metal structure.

7. The dental system according to claim 6, wherein the first support post further comprises a second protruding element protruding from an outer side surface of said first support post, said second protruding element of said first support post configured to be received by a longitudinal recess of an additional rod.

8. The dental system, according to claim 7, wherein the first protruding element and the second protruding element of the first support post are arranged opposite of one another, one on each side of the longitudinal axis of the first support post.

9. The dental system, according to claim 8, wherein the first and second protruding elements of the first support post are arranged at different heights with regard to a base of the first support post.

10. The dental system, according to claim 6, wherein the second support post further comprises a first protruding element protruding from an outer side surface of said second support post, said first protruding element of said second support post configured to be received by a longitudinal blind bore of an additional rod.

11. The dental system, according to claim 10, wherein the first protruding element and the second protruding element of the second support post are arranged opposite of one another, one on each side of the longitudinal axis of the second support post.

12. The dental system, according to claim 11, wherein the first and second protruding elements of the second support post are arranged at different heights with regard to a base of the second support post.

13. The dental system, according to claim 6, wherein the rod comprises at least two segments that are joined by an intermediate articulated connection.

14. The dental system, according to claim 6, wherein the first end of the rod has a conical portion in order to help the movement of the connection to act as a ball joint between the first protruding element and the blind hole.

* * * * *